US012569339B2

(12) United States Patent
Narula et al.

(10) Patent No.:  US 12,569,339 B2
(45) Date of Patent:  Mar. 10, 2026

(54) AORTIC VALVE LITHOTRIPSY BALLOON

(71) Applicant: Narula Health Care Consultants, LLC, Orwigsburg, PA (US)

(72) Inventors: Arvin Narula, San Diego, CA (US); Abdallah Bitar, Denver, CO (US)

(73) Assignee: Narula Health Care Consultants, LLC

( * ) Notice: Subject to any disclaimer, the term of this patent is extended or adjusted under 35 U.S.C. 154(b) by 1119 days.

(21) Appl. No.: 17/306,176

(22) Filed: May 3, 2021

(65) Prior Publication Data

US 2021/0338329 A1      Nov. 4, 2021

Related U.S. Application Data

(60) Provisional application No. 63/018,550, filed on May 1, 2020.

(51) Int. Cl.
| | |
|---|---|
| *A61B 17/22* | (2006.01) |
| *A61F 2/24* | (2006.01) |
| *A61B 17/00* | (2006.01) |
| *A61B 18/00* | (2006.01) |
| *A61B 18/26* | (2006.01) |

(52) U.S. Cl.
CPC .. *A61F 2/2433* (2013.01); *A61B 2017/00783* (2013.01); *A61B 2017/22025* (2013.01); *A61B 2017/22055* (2013.01); *A61B 2017/22062* (2013.01); *A61B 2017/22098* (2013.01); *A61B 2018/00255* (2013.01); *A61B 2018/00369* (2013.01); *A61B 2018/263* (2013.01)

(58) Field of Classification Search
CPC .... A61B 17/22012; A61B 2017/22098; A61B 2017/00783; A61B 2017/22025; A61B 2017/22055; A61B 2017/22062; A61B 18/1492; A61B 2018/00285; A61B 2018/00238; A61B 2018/0025; A61B 2018/00255; A61B 2018/00369; A61B 2018/263; A61B 2018/00232; A61F 2/2433
USPC .......... 606/32–32, 41; 607/98, 99, 101, 104, 607/105, 113, 115, 116, 119
See application file for complete search history.

(56) References Cited

U.S. PATENT DOCUMENTS

| | | | |
|---|---|---|---|
| 10,478,202 B2 | 11/2019 | Adams et al. | |
| 2010/0094209 A1* | 4/2010 | Drasler ............. | A61M 25/1002 604/95.04 |
| 2014/0046353 A1* | 2/2014 | Adams ............. | A61B 17/22012 606/159 |

* cited by examiner

*Primary Examiner* — Thomas A Giuliani
(74) *Attorney, Agent, or Firm* — REISING ETHINGTON, P.C.

(57) ABSTRACT

A balloon aortic lithotripsy assembly for placement adjacent an aortic valve. The balloon aortic lithotripsy assembly includes multiple balloon chambers, a shell, and a shock wave generator. The balloon chambers are arranged to establish an open interior residing inboard of the balloon chambers. The shell is located around the balloon chambers. The shock wave generator can be situated on one or more of the balloon chambers, the shell, or both of the balloon chamber(s) and shell. In use, blood is free to travel through the open interior, and the shock wave generator can produce shock waves that are intended to impinge calcified tissues residing at the aortic valve.

8 Claims, 1 Drawing Sheet

AORTIC VALVE LITHOTRIPSY BALLOON

CROSS-REFERENCE TO RELATED APPLICATION

This application claims the benefit of U.S. Provisional Patent Application No. 63/018,550, filed May 1, 2020.

TECHNICAL FIELD

This disclosure relates generally to a medical device and, more particularly to, balloon valvuloplasty devices with shock wave production capabilities for treating aortic calcification of the heart.

BACKGROUND

Aortic stenosis is caused by calcium build-up and consequential calcification on the aortic valve in a human patient's heart. This can preclude the aortic valve from opening and can further cause turbulent flow. Since the aortic valve does not open well, increased stress is put on the left ventricle or main pumping chamber of the heart. This can cause the heart muscle to increase in size and eventually fatigue. In the past, surgical aortic valve replacement was, for the most part, the only option for most patients. But more recently transcatheter aortic valve replacement (TAVR) has become an option for patients with high, intermediate, and low surgical risk. One issue encountered with transcatheter aortic valve replacement is large areas of calcification which, when developed, can limit expansion of the aortic valve and can also increase the risk of paravalvular leak and annular rupture of the aortic root complex. Moderate or severe paravalvular leak has been shown to worsen long-term outcomes in certain cases.

SUMMARY

In an embodiment, a balloon aortic lithotripsy assembly for placement at or near an aortic valve may include multiple balloon chambers, a shell, and a shock wave generator. The balloon chambers establish an open interior. The shell is located around the balloon chambers. The shock wave generator is capable of producing shock waves at one or more of the balloon chambers. Amid use of the balloon aortic lithotripsy assembly, blood flow travels through the open interior, and the shock wave generator is capable of producing shock waves for impinging calcified tissues at the aortic valve.

In an embodiment, a balloon aortic lithotripsy assembly for placement at or near an aortic valve of a patient's heart may include multiple balloon chambers and a shock wave generator. The balloon chambers establish an open interior. The open interior resides inboard of the balloon chambers. The open interior spans longitudinally through the balloon chambers. The shock wave generator is capable of producing shock waves at one or more of the balloon chambers. The shock wave generator includes one or more electrodes. The electrode(s) is disposed at one or more of the balloon chambers.

In an embodiment, a balloon aortic lithotripsy assembly for placement at or near an aortic valve of a patient's heart may include multiple balloon chambers, a shell, and a shock wave generator. The balloon chambers have a first open end and have a second open end. The balloon chambers establish an open interior. The open interior resides inboard of the balloon chambers. The open interior is defined in part or more by outer surfaces of the balloon chambers. The open interior spans longitudinally through the balloon chambers between the first open end and the second open end. The shell is disposed around the balloon chambers. The shell holds the balloon chambers in place in assembly. The shock wave generator is capable of producing shock waves at one or more of the balloon chambers, at the shell, or at both of the one or more balloon chambers and shell. The shock wave generator includes one or more electrodes. The electrode(s) is disposed at one or more of the balloon chambers, at the shell, or at both of the one or more balloon chambers and shell. Amid use of the balloon aortic lithotripsy assembly, blood flow travels through the open interior of the balloon chambers and between the first and second open ends.

BRIEF DESCRIPTION OF DRAWINGS

The following detailed description of an embodiment is set forth with reference to the accompanying drawings, in which.

DETAILED DESCRIPTION

Figures 1, 2:
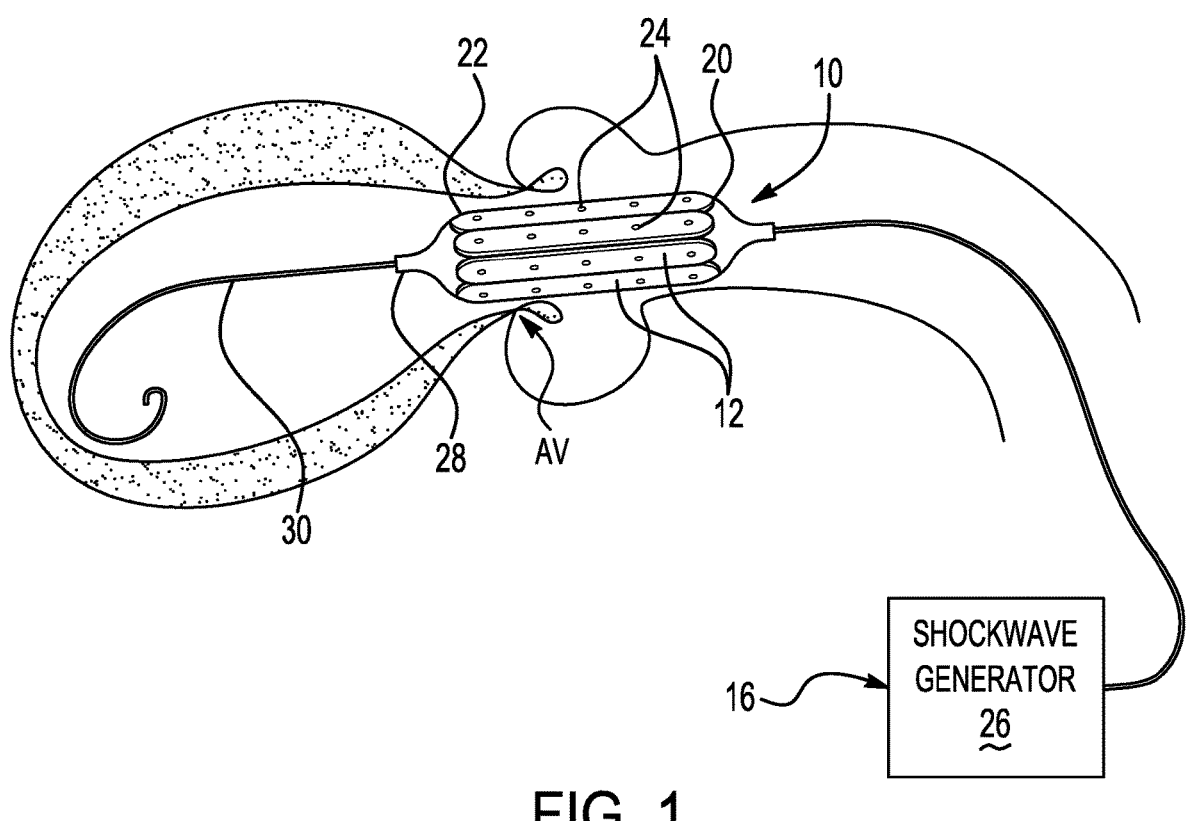
FIG. 1 is a schematic depiction of an embodiment of a balloon aortic lithotripsy assembly, the assembly being shown positioned at an aortic valve of a patient's heart.
FIG. 2 is a sectional view of the balloon aortic lithotripsy assembly of FIG. 1.

The figures present an embodiment of a balloon aortic lithotripsy assembly 10 that is suitable for use in a valvuloplasty medical procedure on a human patient. The balloon aortic lithotripsy assembly 10 is designed and constructed to effect lithotripsy at a heart's aortic valve AV in order to impinge, fracture, and hence disrupt calcific nodules that may be present at or near placement of the balloon aortic lithotripsy assembly 10. Furthermore, unlike past procedures, the balloon aortic lithotripsy assembly 10 eliminates the need for rapid pacing of the patient's heart that has been employed to keep the balloon aortic lithotripsy assembly 10 at the aortic valve AV, giving the operator more time to perform lithotripsy of the calcific nodules. Overall, the balloon aortic lithotripsy assembly 10 furnishes a more effective and compliant positional and placement procedure than previously possible, and provides an increase in annular compliance, thereby reducing perivalvular leak and hence preclusion of the attendant drawbacks. The balloon aortic lithotripsy assembly 10 is employed for use with a human patient.

The balloon aortic lithotripsy assembly 10 can have various designs, constructions, and components in different embodiments. Its precise design, construction, and components can be dictated in part or more on the precise application and intended use and functionality of the balloon aortic lithotripsy assembly 10. In the embodiment of FIGS. 1 and 2, the balloon aortic lithotripsy assembly 10 includes multiple balloon chambers 12, a shell 14, and a shock wave generator 16. Still, in other embodiments the balloon aortic lithotripsy assembly 10 can have more, less, and/or different components, depending upon—among other possible influences—the precise application and intended use and functionality.

The balloon chambers 12, once inflated, constitute the main structural skeleton of the balloon aortic lithotripsy assembly 10. The balloon chambers 12 can be composed of a fiber-based material, as an example, and can be inflated with a suitable liquid medium LM via syringe injection once set in place. In an example, the suitable liquid medium LM is a saline liquid. An individual balloon chamber 12 can have an elongated longitudinal extent from end-to-end, and can have a sectional profile shape that is generally circular, oval, oblong, or the like. The embodiment presented has a total of eight individual balloon chambers 12; in other embodiments not presented, there could be other quantities of balloon chambers. As perhaps illustrated best by FIG. 2, the balloon chambers 12 are arranged in a circumferential and annular manner, and establish an open interior 18 residing and located radially-inboard of the balloon chambers 12 (radially is used herein with respect to the somewhat circular shape of the balloon chambers 12 and of the shell 14). When inflated, neighboring and contiguous balloon chambers 12 abut each other at their sides, as shown in FIG. 2.

The open interior 18 is centrally-located with respect to the balloon chambers 12, and spans longitudinally and lengthwise through the balloon aortic lithotripsy assembly 10 and with respect to the balloon chambers 12 and shell 14. The open interior 18 extends between a first open end 20 and a second open end 22 of the balloon chambers 12. The first and second open ends 20, 22 are established at respective terminal ends of the balloon chambers 12 and provide access for blood flow amid use of the balloon aortic lithotripsy assembly 10. The open interior 18 spans wholly through an axial extent established by the balloon chambers 12 (axial is used herein with respect to the somewhat circular shape of the balloon chambers 12 and of the shell 14). The void constituting the open interior 18 is defined in part by outer surfaces 13 of the balloon chambers 12, as illustrated in FIG. 2. This somewhat hollow central region provided by the open interior 18 facilitates cardiac blood flow therethrough and between the first and second open ends 20, 22 amid placement and position procedures of the balloon aortic lithotripsy assembly 10.

The shell 14 is located around the balloon chambers 12 and, in this embodiment, serves as a housing to keep the balloon chambers 12 in their intended locations for establishment of the open interior 18. The shell 14 surrounds the balloon chambers 12 and holds the balloon chambers 12 in place. When inflated, the balloon chambers 12 can come into contact with an inside surface of the shell 14, as depicted in FIG. 2. The shell 14, shown in sectional profile in FIG. 2, can have a circular or somewhat oval shape. The shell 14 can be composed of a fiber-based material, or could be composed of another type of suitable material. The shell 14 extends wholly circumferentially over the balloon chambers 12, leaving axial openings at the first open end 20 and the second open end 22 of the balloon chambers 12.

The shock wave generator 16 serves to produce pulsations in the form of acoustic shock waves. The shock waves emanate from one or more electrodes 24 situated and disposed at various sites on the balloon chambers 12 and/or on the shell 14. In one example, the electrode(s) 24 may each include a pair of individual electrodes with a small gap defined therebetween. A voltage supplied at the pair of individual electrodes causes an electrical arc to jump the gap between them. The electrode(s) 24 can have an attachment to the respective component and structure at its particular location. The precise location of the electrode(s) 24 may be dependent upon, among other possible considerations, the desired intensity of the shock waves produced and emitted to the subject calcium build-up and calcification; in some instances, it has been observed that the intensity of the shock wave may diminish at increased distances from shock wave origination.

FIG. 2 depicts some example sites for deployment of the electrode(s) 24, but is not meant to be exhaustive. In one embodiment the electrode(s) 24 can be carried by the shell 14, on the interior or exterior thereof (FIG. 2 depicts the exterior possibility). In another embodiment the electrode(s) 24 can be carried by one or more of the balloon chambers 12. In a particular embodiment, the electrode(s) 24 are located and positioned at an interior 25 and at an inside of one or more the balloon chambers 12 (this particular example is depicted in FIG. 2); the electrode(s) 24 reside within the liquid medium LM upon inflation of the balloon chambers 12 in this example. Here, when an electrical arc jumps a gap between electrodes, gas bubbles in the liquid medium LM are created that rapidly expand and collapse, producing shock waves therefrom. In an even more particular example, a first electrode of the electrode(s) 24 can reside in the interior 25 of a first balloon chamber of the balloon chambers 12, and a second electrode of the electrode(s) 24 can reside in the interior 25 of a second balloon chamber of the balloon chambers 12. The duration of the shock waves produced can vary, and may be a few microseconds, for example. In yet another embodiment a first set of electrodes 24 can be carried by the shell 14 and a second separate and distinct set of electrodes 24 can be carried by one or more of the balloon chambers 12.

Furthermore, the shock wave generator 16 can include a voltage power source 26 that electrically communicates with the electrodes 24 for pulsation production purposes. The voltage supplied can range between approximately one-hundred volts (100 V) to three-thousand volts (3,000 V) in an example; still, the voltage supplied can vary in other examples. The electrical communication can be effected via wiring, for example. The wiring can be routed along a wire (introduced below) for positioning and placement of the balloon chambers 12 and shell 14 at the patient's aortic valve AV. Still, and while lacking specific depiction, the shock wave generator 16 can include other components and arrangements to effect shock wave generation. For example, in various embodiments, a series resistance can be provided, a capacitance can be provided, and/or a high voltage switch can be provided.

Furthermore, a port 28 may be provided in order to track and guide the balloon chambers 12 and shell 14 over a wire 30 for maintaining position and placement of the balloon chambers 12 and shell 14 at the left ventricle of the patient's heart, and ultimately for positioning and placement at the heart's aortic root complex. The wire 30 can have a diameter of 0.035 inches, for example, or could have another value.

During use, the balloon aortic lithotripsy assembly 10 is employed for utilization in a valvuloplasty medical procedure. Initially, the balloon aortic lithotripsy assembly 10 is brought to the heart's aortic root complex via a catheter procedure. The balloon chambers 12 are inflated at the patient's aortic valve AV. Once established, the open interior 18 accommodates cardiac blood flow through the balloon aortic lithotripsy assembly 10 and its components. Blood flow travels between the first open end 20 and the second open end 22 of the balloon chambers 12 via the open interior 18. Because of this accommodation and accompanying blood flow travel, rapid pacing of past procedures need not be performed, providing increased stability and a lengthened time period of placement and positioning of the balloon aortic lithotripsy assembly 10 at the aortic valve AV. The undesired rhythmic state of the heart accompanying rapid pacing can hence altogether be avoided with the use of the balloon aortic lithotripsy assembly 10. Furthermore, lithotripsy treatment is carried out as part of the valvuloplasty medical procedure. The lithotripsy treatment involves use of the shock wave generator 16 to emit pulsations in the form of shock waves to impinge, fracture, and hence disrupt calcium build-up—particularly areas of heavy calcification—that may be present and may reside at or near placement of the balloon aortic lithotripsy assembly 10. In an example, the shock waves produced impinge and fracture calcified tissues at the aortic valve AV. The disruption can cause an alteration to the calcium nodules, such as breakage and/or softening and/or loosening, and can ultimately provide enhanced compliance of the aortic annulus. Depending on the location of the electrodes 24 of the shock wave generator 16, the shock waves produced may propagate through the liquid medium LM of the inflated balloon chambers 12.

It is to be understood that the foregoing description is of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "for instance," and "such as," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A balloon aortic lithotripsy assembly for placement at or adjacent an aortic valve, the balloon aortic lithotripsy assembly comprising:
   a plurality of balloon chambers, said plurality of balloon chambers arranged circumferentially with respect to one another, said plurality of balloon chambers establishing an open interior residing radially-inboard of said plurality of balloon chambers;
   a shell located around said plurality of balloon chambers; and
   a shock wave generator capable of producing shock waves at at least one of said plurality of balloon chambers, said shock wave generator including a plurality of electrodes disposed within an interior of said at least one of said plurality of balloon chambers and disposed on an exterior of said shell;
   wherein, amid use of the balloon aortic lithotripsy assembly, blood flow travels through said open interior and said shock wave generator is capable of producing shock waves for impingement upon calcified tissues at the aortic valve.

2. The balloon aortic lithotripsy assembly as set forth in claim 1, wherein said open interior is defined at least in part by outer surfaces of said plurality of balloon chambers.

3. The balloon aortic lithotripsy assembly as set forth in claim 1, wherein said open interior spans longitudinally through the balloon aortic lithotripsy assembly between a first open end of said plurality of balloon chambers and a second open end of said plurality of balloon chambers.

4. The balloon aortic lithotripsy assembly as set forth in claim 3, wherein, amid use of the balloon aortic lithotripsy assembly, blood flow travels through said open interior and between said first open end and said second open end of said plurality of balloon chambers.

5. A balloon aortic lithotripsy assembly for placement at or adjacent an aortic valve of a patient's heart, the balloon aortic lithotripsy assembly comprising:
   a plurality of balloon chambers, said plurality of balloon chambers establishing an open interior, said open interior residing inboard of said plurality of balloon chambers, said open interior spanning longitudinally through said plurality of balloon chambers;
   a shell disposed around said plurality of balloon chambers, said shell holding said plurality of balloon chambers in place; and
   a shock wave generator capable of producing shock waves at at least one of said plurality of balloon chambers, said shock wave generator including a plurality of electrodes disposed at said at least one of said plurality of balloon chambers within an interior thereof and disposed on an exterior of said shell;
   wherein said open interior spans longitudinally through said plurality of balloon chambers between a first open end of said plurality of balloon chambers and a second open end of said plurality of balloon chambers, and wherein, amid use of the balloon aortic lithotripsy assembly, blood flow travels through said open interior and between said first open end of said plurality of balloon chambers and said second open end of said plurality of balloon chambers.

6. The balloon aortic lithotripsy assembly as set forth in claim 5, wherein said plurality of balloon chambers make abutment with one another, said plurality of balloon chambers having outer surfaces that establish said open interior.

7. The balloon aortic lithotripsy assembly as set forth in claim 5, wherein said plurality of balloon chambers includes a first balloon chamber and a second balloon chamber, and said plurality of electrodes includes a first electrode and a second electrode and a third electrode, wherein said first electrode is disposed in an interior of said first balloon chamber and said second electrode is disposed in an interior of said second balloon chamber and said third electrode is disposed on said exterior of said shell.

8. A balloon aortic lithotripsy assembly for placement at or adjacent an aortic valve of a patient's heart, the balloon aortic lithotripsy assembly comprising:
   a plurality of balloon chambers, said plurality of balloon chambers having a first open end and a second open end, said plurality of balloon chambers establishing an open interior residing inboard of said plurality of balloon chambers, said open interior defined at least in part by outer surfaces of said plurality of balloon chambers, said open interior spanning longitudinally through said plurality of balloon chambers between said first open end and said second open end;
   a shell disposed around said plurality of balloon chambers, said shell holding said plurality of balloon chambers in place; and
   a shock wave generator capable of producing shock waves at both of at least one of said plurality of balloon chambers and at said shell, said shock wave generator including a plurality of electrodes disposed within an interior of said at least one of said plurality of balloon chambers and disposed on an exterior of said shell.

* * * * *